United States Patent [19]

Singh et al.

[11] 4,361,518

[45] Nov. 30, 1982

[54] MANUFACTURE OF ISOCYANATES

[75] Inventors: Balwant Singh; William A. Henderson, Jr., both of Stamford, Conn.

[73] Assignee: American Cyanamid Company, Stamford, Conn.

[21] Appl. No.: 331,696

[22] Filed: Dec. 17, 1981

[51] Int. Cl.³ .......................................... C07C 118/00
[52] U.S. Cl. ................................................ 260/453 P
[58] Field of Search .................................... 260/453 P

[56] References Cited

U.S. PATENT DOCUMENTS 3,290,350 12/1966 Hoover ............................. 260/453 P
4,130,577 12/1978 Nagato et al. .................... 260/453 P Primary Examiner—Dolph H. Torrence
Attorney, Agent, or Firm—Steven J. Hultquist

[57] ABSTRACT

A process for production of tertiary benzyl isocyanates by reaction at low temperatures of the corresponding halides with an excess of isocyanic acid.

17 Claims, No Drawings

MANUFACTURE OF ISOCYANATES

This invention relates to the manufacture of tertiary benzylic isocyanates, particularly isocyanates such as the tetramethylxylyenediisocyanates (TMXDI) and chloroisopropyldimethylbenzyl isocyanates, and in particular provides a process for the preparation of such isocyanates from the corresponding halides.

Isocyanates are a well known and valuable class of compounds. In particular meta- and para-TMXDI are useful for reaction with a wide variety of polyols to give polyurethanes which are either rigid or flexible and which can be endowed with a wide variety of properties. Thus such polyurethanes can be formed into rigid and flexible foamed articles, sheets, high density sheets and articles of various shapes. The light stability of the polyurethanes makes them extremely useful in coatings and other applications where light stability is desirable, e.g. light stable RIM elastomers.

Tertiary benzylic isocyanates, such as TMXDI have heretofore been manufactured by phosgenation of the corresponding organic amines, by reaction of the corresponding olefins with isocyanic acid (U.S. Pat. No. 3,290,350) and by reaction of the corresponding halides with an alkali metal isocyanate (U.S. Pat. No. 4,130,577).

The phosgenation route suffers disadvantages from the commercial standpoint in that phosgene itself is an unsafe material and difficult to handle. In addition the organic amines are difficult to produce. The olefin route suffers the disadvantages that the yields are poor and that large amounts of olefin and isocyanic acid are lost through selfpolymerization. On the other hand, while the reaction of the halide with the alkali metal isocyanate can provide high yields, the reaction times are long and the halogen is completely lost as the alkali metal halide, recoverable only at great expense.

It is thus an important object of this invention to provide a process for the production of tertiary benzylic isocyanates which can be made to operate on a commercially economic basis with high yields of the desired product. It is a further object of the invention to provide such a process which can be operated at relatively fast rates conducive to continuous production. It is yet another object of this invention to provide such a process in which excess reactants are readily recoverable.

Thus in accordance with this invention tertiary benzyl isocyanates are produced by reaction of the corresponding halide with isocyanic acid, HNCO, utilizing an excess of isocyanic acid in solution in an aromatic hydrocarbon, halogenated hydrocarbon, or aliphatic hydrocarbon solvent, such as toluene, xylenes, chlorobenzene, orthodichlorobenzene, heptane, benzene, methylene dichloride and the like. Generally the solvent is an aprotic or non-polar solvent which is a solvent both for the starting halide and for the isocyanic acid.

The reaction proceeds at relatively low temperatures, almost instantaneously in the presence of suitable catalyst. The reaction will proceed, however somewhat more slowly, even in the total absence of catalyst and even at relatively low temperatures. Preferably the reaction is carried out at temperatures on the order of $-10°$ to $10°$ C. High and lower temperatures can be utilized. Higher temperatures, however, favor polymerization of isocyanic acid to form solids while lower temperatures reduce the speed reaction.

It is preferred but not necessary that the reactants should be substantially anhydrous. Small amounts of water above approximately 1000 ppm tend to make the reaction sluggish.

Tertiary benzyl halides which can be reacted with isocyanic acid in accordance with this invention have the halogen substituent on a tertiary carbon atom of an alkyl substituent of an aromatic moiety, for example, a 2-chloroisopropyl benzene, such as:

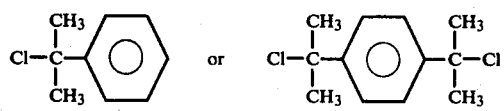

The aromatic moiety can also be a fused ring moiety, such as naphthalene etc. The aromatic moiety can have other, non-reactive substituents such as alkyl and alkoxy substituents, halogens such as chlorine, bromine and fluorine, and certain non-reactive halo-substituted alkyls, e.g., $CF_3$. The haloalkyl substituent can be varied provided the halogen is attached to a tertiary carbon which is attached to an aromatic moiety. Thus haloalkyl aromatic compounds of the generalized formula [1] are suitable for reaction with isocyanic acid to substitute the isocyanto radical for the halide.

in which:

X is a halogen atom, Cl, Br, (I) and $R_1$ and $R_2$ are alkyl groups having from 1 to 3 carbon atoms and $R_3$ is aromatic hydrocarbon group such as phenyl, biphenyl, or naphthyl or such an aromatic hydrocarbon group having substituents such as halogen atoms, methyl or methoxy groups, nitro groups, or

substituents.

Such halide compounds are readily obtained in high yield by synthesis from the corresponding olefin and HCl. The reaction of the halide with excess isocyanic acid results in the formation of the isocyanate and hydrogen chloride. The latter combines with excess isocyanic acid to produce carbamoyl chloride. Excess isocyanic acid and carbamoyl chloride are recoverable by distillation or other means and can be recycled.

The preferred catalysts are zinc chloride, zinc bromide and zinc iodide. Other Lewis acids, such as bismuth trichloride and bismuth tribromide have also been found to exhibit substantial catalytic activity. Ferric chloride and stannous chloride have shown weak catalytic activity. On the other hand boron trichloride, mercuric chloride, aluminum tribromide, aluminum trichloride, ferrous chloride, zirconium chloride and cuprous chloride have been found to exhibit little or no catalytic activity.

Other zinc salts which have been found effective as catalysts in the process of this invention are zinc neodecanoate, zinc octanoate, zinc fluoride, and zinc dodecylbenzenesulfonate.

The catalyst can be added in solid form, or it can be slurried in a suitable diluent or dissolved in a suitable solvent and added to the reaction mixture. Preferably the catalyst is added in solution form to a precooled solution of the isocyanic acid over the relatively short time required for reaction, for example, 90 seconds. All catalysts showing activity have been found soluble in ether or acetone and have been used in solution. The preferred solvent for zinc chloride catalyst is diethylether. Basic solvents, such as pyridine, are to be avoided, as the isocyanic acid is almost completely lost in polymerization to cyanuric acid.

The proportion of isocyanic acid is generally in excess of the halide on a stoichiometric basis and preferably is from 2 to 6 moles of isocyanic acid per halogen atom. The proportion of the preferred catalyst is preferably about 0.025 mole per halogen atom but can be varied between 0.01 and 0.1 mole with good results.

For a more complete understanding of the practical application of this invention reference is made to the following examples:

EXAMPLE I

Para di(2-chloroisopropyl)benzene (para-TMXDC) was prepared in 2 M solution in toluene dried over 3 A molecular sieve. A 3.8 M solution of isocyanic acid (HNCO) was also prepared in toluene dried over a molecular sieve. Anhydrous zinc chloride catalyst was prepared in a 1 M solution in anhydrous diethylether.

11.5 mmoles of isocyanic acid solution was placed in a 20 ml reaction vessel cooled in an ice bath to 0° C. Agitation was provided using a magnetic stirrer. Two mmoles and 0.1 mmoles of the para-di(2-chloroisopropyl)benzene and zinc chloride solutions, respectively, were simultaneously added using two separate syringe pumps over the course of 90 seconds. The reaction mixture was stirred and kept in the ice bath over the whole course of the reaction period. Aliquots of the reaction were then removed and analyzed.

Analysis for the organic products was by gas chromatography and for the isocyanic acid by titration. The isocyanic acid analysis was conducted by extracting an aliquot of the reaction mixture with sodium hydroxide solution to give sodium isocyanate and conversion of the isocyanate to ammonia by reaction with hydrochloric acid. The solution was then basified and ammonia determined with an ammonia specific electrode. The by-product carbamoyl chloride was also converted to ammonia and analyzed as such.

The results are shown in Table I. 98% of the dichloride was consumed with yields of 9% of the monochloride-monoisocyanate and 79% of the diisocyanate, (TMXDI), based on the initial dichloride. The yield of diisocyanate was 87%, based on the isocyanic acid consumed. Four additional runs repeating the procedure of Example I gave similar results with yields of diisocyanate from 75 to 76%, based on the dichloride consumed.

EXAMPLES II–XI

Results Shown in Table I

EXAMPLE II

The procedure of Example I was repeated, except the zinc chloride solution was added all at once and the temperature was 45° C.

EXAMPLE III

The procedure of Example I was repeated, except that the zinc chloride was added last and all at once. The results shown in Table I are an average of three runs.

EXAMPLE IV

The procedure of Example III was repeated but diluted with toluene from 4.4 ml to 16.4 ml.

EXAMPLE V

The procedure of Example I was repeated except the zinc chloride was in acetone solution.

EXAMPLE VI–VIII

The procedure of Example was repeated, except the proportion of isocyanic acid to para-TMXDC was 4.2 (Example VI), 8.1 (Example VII) and 12.2 (Example VIII).

EXAMPLES IX AND X

The procedure of Example I was repeated, except the amount of zinc chloride was 0.05 mmoles (Example IX) and 0.2 mmoles (Example X).

EXAMPLE XI

The procedure of Example I was repeated, except methylene chloride was substituted as the solvent for the dichloride and the isocyanic acid.

TABLE I

| Example No. | Unreacted Dichloride | Yield, Wt. % Chloro-isocyanate | TMXDI | Yield, Wt. % Based On Consumption Of Di-chloride | HNCO |
|---|---|---|---|---|---|
| I | 2 | 9 | 79 | 80 | 87 |
| II | 8 | 24 | 24 | 26 | 10 |
| III | 3 | 10 | 55 | 56 | — |
| IV | 50 | 18 | 3 | 6 | — |
| V | 17 | 24 | 41 | 50 | — |
| VI | 27 | 20 | 21 | 29 | 41 |
| VII | 13 | 20 | 38 | 39 | 50 |
| VIII | 9 | 20 | 60 | 66 | 67 |
| IX | 2 | 14 | 67 | 68 | — |
| X | 4 | 12 | 73 | 76 | — |
| XI | 7 | 20 | 58 | 62 | 62 |

Increasing the scale of the process lengthened the time of the reaction as the dichloride and catalyst had to be added more slowly to hold the temperature under 10° C. At 20 times the scale with addition of dichloride and zinc chloride over ten minutes, maximum temperature was 5° C., and the diisocyanate yield was 72%, 75% based on the dichloride consumed.

EXAMPLE XII

Meta di(2-chloroisopropyl)benzene was reacted with isocyanic acid in toluene solution, following the procedure of Example I, using 2 mmoles of the dichloride and a ratio of dichloride to isocyanic acid to zinc chloride of 1:6.5:0.05 in a bath maintained at −10° C. with addition of catalyst and dichloride over a 1.5 minute period of time. The yield of an average of four runs was 8% of the monochloride-monoisocyanate and 85% of the diisocyanate, 92% diisocyanate calculated on the basis of dichloride consumed, and 86% calculated on the basis of isocyanic acid consumed.

EXAMPLE XIII

The procedure of Example I was followed omitting the catalyst with the following results:

TABLE II

| Time, hrs. | Yields, wt % | | Yield wt % of TMXDI Based on Consumption of | |
|---|---|---|---|---|
| | Chloro-isocyanate | TMXDI | DICHLORIDE | HNCO |
| 0.06 | 0.3 | 0 | 0 | 0 |
| 1 | 28 | 1 | 2 | — |
| 2 | 38 | 5 | 7 | 11 |
| 3.5 | 40 | 10 | 12 | — |
| 5 | 40 | 14 | 16 | 21 |

A continuous, backstirred reactor was set up with provision for addition of a reactant stream of isocyanic acid and para di(2-chloroisopropyl)benzene in toluene solution and a zinc chloride catalyst stream in ether, utilizing the concentrations and proportions of Example I. The reactor was provided with agitation by a magnetic stirrer, and was cooled with a salt/ice bath held at $-10°$ C. The dichloride and isocyanic acid streams were premixed just before entering the reactor to minimize crystallization of the dichloride upon contact with the cold reactor. The temperature of the reaction mixture was 0° C., and the residence time was 3.6 minutes. The effluent was diluted with cold toluene for chromatographic analysis or was extracted with caustic solution for analysis for isocyanic acid. The results were as follows:

TABLE III

| Residence Times | Temp. °C. | Yields, wt % | | Yields, wt % based on Consumption of | |
|---|---|---|---|---|---|
| | | Chloro-isocyanate | TMXDI | DICHLORIDE | HNCO |
| 3 | 0 | 11 | 80 | 94 | 68 |
| 4 | 1 | 11 | 78 | 92 | 64 |
| 6 | 1 | 11 | 78 | 92 | 63 |

U.S. Pat. No. 4,130,577 described the reaction of alkali metal isocyanate with organic halides in organic solvents to make organic isocyanates and by-product metal chlorides. The substitution of isocyanic acid instead of metal halides in the reactions that were described in that patent will not result in an eqivalent yield of organic isocyanate. The yield of isocyanate, when there is any, will be only very small. Example 33 in the '577 patent described a reaction which produced a 66% yield of tetramethylxylylene diisocyanate (TMXDI). When we reproduced the same reaction except using HNCO instead of NaNCO, there was no production of any TMXDI. If alkali metal isocyanate were substituted instead of isocyanic acid in the reaction with organic chlorides of the present invention, the results would not be the same. Instead of consuming two moles of metal isocyanate reactant and producing one mole of soluble carbamyl chloride (for each chloride atom reacted), only one mole of the metal isocyanate would be consumed and an insoluble metal halide by-product would be produced.

We claim:
1. A process for the production of tertiary benzyl isocyanates which comprises reacting a halide of the formula

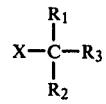

in which X represents a halogen atom, $R_1$ and $R_2$ represent alkyl groups of 1 to 3 carbon atoms and $R_3$ represents an aromatic group such as a phenyl, bisphenyl or naphthyl group or a substituted phenyl, biphenyl or naphthyl group having halogen, methyl, methoxy substituents or substituents of the formula

with a stoichiometric excess of isocyanic acid in a solution in a solvent for said halide and isocyanic acid.

2. A process according to claim 1 in which said reaction is carried out in the presence of a catalyst effective to promote the reaction of halide and isocyanic acid to form the isocyanate.

3. A process according to claim 2 in which the catalyst is a zinc salt.

4. A process according to claim 2 in which the catalyst is zinc chloride.

5. A process according to claim 2 in which the catalyst is zinc octanoate.

6. A process according to claim 1 in which the solvent is toluene.

7. A process according to claim 3 in which the solvent is toluene.

8. A process according to claim 1 in which the halide is a di(2-chloroisoproypl)benzene.

9. A process according to claim 3 in which the halide is a di(2-chloroisopropyl)benzene.

10. A process according to claim 1 in which the reaction temperature is between $-10°$ and 10° C.

11. A process according to claim 3 in which the reaction temperature is between $-10°$ and 10° C.

12. A process according to claim 1 in which the proportion of isocyanic acid is from 2 to 10 moles per halogen atom of the halide.

13. A process according to claim 3 in which the proportion of isocyanic acid is from 2 to 10 moles per halogen atom of the halide.

14. A process according to claim 1 in which the solvent is methylene dichloride.

15. A process according to claim 3 in which the solvent is methylene dichloride.

16. A process according to claim 5 in which the halide is para di(2-chloroisopropyl) benzene.

17. A process according to claim 5 in which the halide is meta di(2-chloroisopropyl) benzene.

* * * * *